United States Patent
Ko et al.

(10) Patent No.: US 9,828,442 B2
(45) Date of Patent: Nov. 28, 2017

(54) **METHOD TO PREPARE *HIRSUTELLA SINENSIS* POLYSACCHARIDES POSSESSING INSULIN-SENSITIZING PROPERTIES AND APPLICATIONS THEREOF**

(71) Applicant: Chang Gung Biotechnology Corp., Taipei (TW)

(72) Inventors: Yun-Fei Ko, Taipei (TW); Jan Martel, Taipei (TW); Jian-Ching Liau, Taipei (TW); I-Te Chang, Taipei (TW); Chien-Sheng Lee, Taipei (TW); Wei-Chang Wang, Taipei (TW); Chen-Yaw Chiu, Taipei (TW); Chih-Jung Chang, Taipei (TW); Chuan-Sheng Lin, Taipei (TW); Tsung-Ru Wu, Taipei (TW); Chia-Chen Lu, Taipei (TW); David Marcelo Ojcius, Taipei (TW); Hsin-Chih Lai, Taipei (TW); Ding-E Young, Taipei (TW)

(73) Assignee: Chang Gung Biotechnology Corp., Taipei (TW)

( * ) Notice: Subject to any disclaimer, the term of this patent is extended or adjusted under 35 U.S.C. 154(b) by 184 days.

(21) Appl. No.: 14/855,143

(22) Filed: Sep. 15, 2015

(65) Prior Publication Data
US 2016/0361341 A1    Dec. 15, 2016

(30) Foreign Application Priority Data
Jun. 11, 2015   (TW) .............................. 104118931 A

(51) Int. Cl.
  *A61K 36/00* (2006.01)
  *C08B 37/00* (2006.01)
  *A61K 36/062* (2006.01)

(52) U.S. Cl.
  CPC ........ *C08B 37/0003* (2013.01); *A61K 36/062* (2013.01); *A61K 2236/00* (2013.01)

(58) Field of Classification Search
  CPC ...................................... A61K 36/00
  See application file for complete search history.

(56) References Cited

U.S. PATENT DOCUMENTS

2011/0028428 A1*  2/2011  Wong ................... A61K 31/715
                                                  514/54

FOREIGN PATENT DOCUMENTS

CN       103961534 A  *  8/2014

OTHER PUBLICATIONS

Liu et al, Effect of polysaccharides from cultured mycelium of Cordyceps sinensis on insulin resistance in T2DM mice. Yiyao Daobao (2011), 30(1), 5-8.*

* cited by examiner

*Primary Examiner* — Qiuwen Mi
(74) *Attorney, Agent, or Firm* — WPAT, P.C., Intellectual Property Attorneys; Anthony King

(57) ABSTRACT

The present invention provides a method to prepare polysaccharides from *Hirsutella sinensis*. The prepared polysaccharides can reduce hyperglycemia and insulin resistance, and can therefore be used to prevent and treat type 2 diabetes and related conditions.

9 Claims, 9 Drawing Sheets

METHOD TO PREPARE *HIRSUTELLA SINENSIS* POLYSACCHARIDES POSSESSING INSULIN-SENSITIZING PROPERTIES AND APPLICATIONS THEREOF

CROSS-REFERENCE TO RELATED APPLICATION

This application claims priority of Taiwan patent application No. 104118931, filed on Jun. 11, 2015, the content of which is incorporated herein in its entirety by reference.

BACKGROUND OF THE INVENTION

1. Field of the Invention

The present invention relates to compositions and methods for improving insulin sensitivity. Specifically, the invention provides methods for improving insulin sensitivity by using a polysaccharide isolated from *Hirsutella sinensis* as well as methods for preparing the polysaccharides.

2. The Prior Art

Traditional Chinese medicine has been used for several thousands of years in Asian countries. One class of traditional remedies consists of medicinal mushrooms that include *Antrodia cinnamomea, Agaricus blazei* Murrill, *Ganoderma lucidum*, and *Ophiocordyceps sinensis*. These mushrooms contain a wide range of immuno-modulatory and bioactive compounds. The medicinal mushroom *Ophiocordyceps sinensis* has a long history of use to promote health and longevity. Recent work has identified that the anamorph (or mycelium) of *O. sinensis* fruiting bodies is *Hirsutella sinensis*. Extracts of *O. sinensis* fruiting bodies and *H. sinensis* mycelium have been shown to produce various effects on laboratory animals, including showing anti-fatigue, anti-inflammatory, kidney-protecting, and libido-enhancing properties.

Type 2 diabetes mellitus is a disease characterized by abnormal regulation of blood glucose levels. If left uncontrolled for a prolonged period of time, this condition may lead to several complications, including cardiovascular disease, eye damage, foot ulcers, kidney failure, and stroke. In developed countries, the high prevalence of diabetes is currently a major threat to public health, with approximately 387 million diabetic people worldwide. Prevention of diabetes therefore represents a major challenge.

During the early stage of type 2 diabetes, human peripheral tissues, including the liver, muscles, and adipose tissues, show reduced sensitivity to insulin. At this stage, a number of treatments can be used to stabilize blood glucose levels, including diet monitoring, regular exercise, and medications. For example, metformin is a synthetic drug that decreases hyperglycemia by suppressing glucose production by the liver; by increasing sensitivity to insulin in peripheral tissues; and by decreasing absorption of glucose from food. However, metformin and other anti-diabetic medications produce many side-effects that may limit treatment efficacy and patient compliance.

In view of the growing incidence of diabetes in the human population and the difficulties observed with the prevention and treatment of this condition, there is a need for alternative measures to prevent, treat or control this debilitating disease. New measures that can be introduced in the diet without requiring important changes in lifestyle and without producing severe toxicity or adverse effects on health are especially needed.

SUMMARY OF THE INVENTION

The present invention provides a method for improving insulin sensitivity comprising the administration of an effective amount of a polysaccharide extracted from *Hirsutella sinensis* to a subject, wherein the polysaccharide is isolated from a water extract of *H. sinensis* mycelium and contains at least mannose, glucose, and galactose. The *H. sinensis* polysaccharide further contains fucose, rhamnose, arabinose, glucosamine, and galactosamine. In one embodiment of the present invention, a weight ratio of the fucose, rhamnose, arabinose, glucosamine, galactose, glucose, mannose, and galactosamine in the polysaccharide ranges from 3:3:1:4:23:12:50:0.2 to 4:4:2:5:24:13:51:0.6. The polysaccharide has a molecular weight ranging from 15,776 Da to 1,231,969 Da, an average molecular weight of 312 kDa, and a polydispersity index of 7.475. The *H. sinensis* polysaccharide reduces blood insulin and blood glucose levels in a subject. In one embodiment of the present invention, the effective amount of *H. sinensis* polysaccharide ranges from 0.001 mg/kg to 1 g/kg of body weight. Preferably, the effective daily amount or dosage of *G. lucidum* polysaccharide given to a human subject (with an average weight of 70 kg) is 4.53 g (0.0646 g per kilogram of body weight).

In another aspect, the present invention provides a method for preparing the *H. sinensis* polysaccharide, comprising: extracting *H. sinensis* mycelium with water; inducing the formation of a precipitate by adding an alcohol; separating the precipitate by centrifugation; and fractionating the precipitate by filtration, wherein, (a) mixing *H. sinensis* mycelium with water to give a first mixture; incubating the first mixture for a first predetermined time under low-speed rotation to obtain a supernatant; and concentrating the supernatant to obtain a concentrated *H. sinensis* water extract; (b) adding an alcohol to the concentrated *H. sinensis* water extract to give a second mixture; allowing the second mixture to stand for a second predetermined time to obtain a precipitate of crude *H. sinensis* polysaccharide; (c) isolating the precipitate by centrifugation; and fractionating the precipitate by tangential flow filtration (TFF) to obtain a *H. sinensis* polysaccharide with insulin-sensitizing properties.

In one embodiment of the present invention, for step (a), the *H. sinensis* mycelium is mixed with water at a ratio of 5% (w/v) and the supernatant is concentrated using a vacuum concentrator. For step (b), the alcohol consists of 95% (v/v) ethanol, each volume of the 20% (w/v) concentrated *H. sinensis* water extract is mixed with five volumes of 95% ethanol, and the second predetermined time is at least 16 hours. For step (c), the crude *H. sinensis* polysaccharide extract (precipitate) is fractionated using TFF with a 0.2-nm hollow fiber membrane and 10-to-300-kDa cassette membranes (50 cm$^2$, polyethersulfone, PES).

The *H. sinensis* polysaccharide of the present invention can reduce hyperglycemia and improve insulin sensitivity in humans and animals. The polysaccharide can therefore be utilized as a medicine, a health supplement, a food, or a drink for the prevention and treatment of type 2 diabetes mellitus and related diseases involving disturbed blood sugar homeostasis, such as insulin resistance and metabolic syndrome.

The present invention is further explained in the embodiments, drawings, and examples given below. The examples should not, however, be considered to limit the scope of the invention, and it will be understood that modifications can

DETAILED DESCRIPTION OF THE PREFERRED EMBODIMENT

The accompanying drawings are included to further demonstrate some aspects of the present invention, which can be better understood by reference to one or more of these drawings, in combination with the detailed description of the embodiments presented herein. The drawings illustrate embodiments of the present invention and, together with the description, serve to explain the principles of the invention.

Definition

The "effective dosage" or "effective amount" described in the present disclosure represents the dosage of polysaccharide sub-fraction isolated from *H. sinensis* that can produce glucose-lowering or insulin-sensitizing effects in animals and humans. The appropriate effective dosage may vary depending on the organism or individual treated but can be determined experimentally using various techniques, including a dose escalation study.

The data presented in the present disclosure are approximated, experimental values that may vary within a range of ±20%, preferably ±10%, and most preferably ±5%.

The present invention provides *H. sinensis* polysaccharide sub-fractions possessing insulin-sensitizing properties. Through experimentations, the *H. sinensis* polysaccharide sub-fractions of the present invention are proven to be able to effectively reduce blood glucose levels in a subject fed a HFD and submitted to OGTT or ITT challenges. Given that subjects fed HFD show reduced sensitivity to insulin and that OGTT and ITT tests reflect the ability of peripheral tissues (e.g., liver, muscles) to absorb glucose from the blood via insulin activity, the experimental results shown in the present disclosure indicate that the *H. sinensis* polysaccharide sub-fractions possess insulin-sensitizing effects. Generally, the polysaccharide sub-fractions described herein can be administered to mammals and humans daily at a dose of 0.001 mg/kg to 1 g/kg of body weight and can effectively reduce insulin resistance in a subject. Details of the invention are provided below.

Characterization of the *H. sinensis* polysaccharide sub-fraction of the present invention is presented first, followed by experimentations showing the effects of the isolated polysaccharide sub-fractions on OGTT and ITT in mice.

Example 1

Preparation of *H. sinensis* Water Extracts and Polysaccharide Sub-Fractions

In the present invention, *H. sinensis* polysaccharides can effectively reduce hyperglycemia and promote insulin sensitivity. The *H. sinensis* poly saccharides described in the present invention can be added to the diet as a drink, a health supplement, or a food, without requiring significant lifestyle changes for the subject, or without producing toxicity or other unfavorable health conditions.

1.1 Preparation of *H. sinensis* Water Extracts

Figure 1:
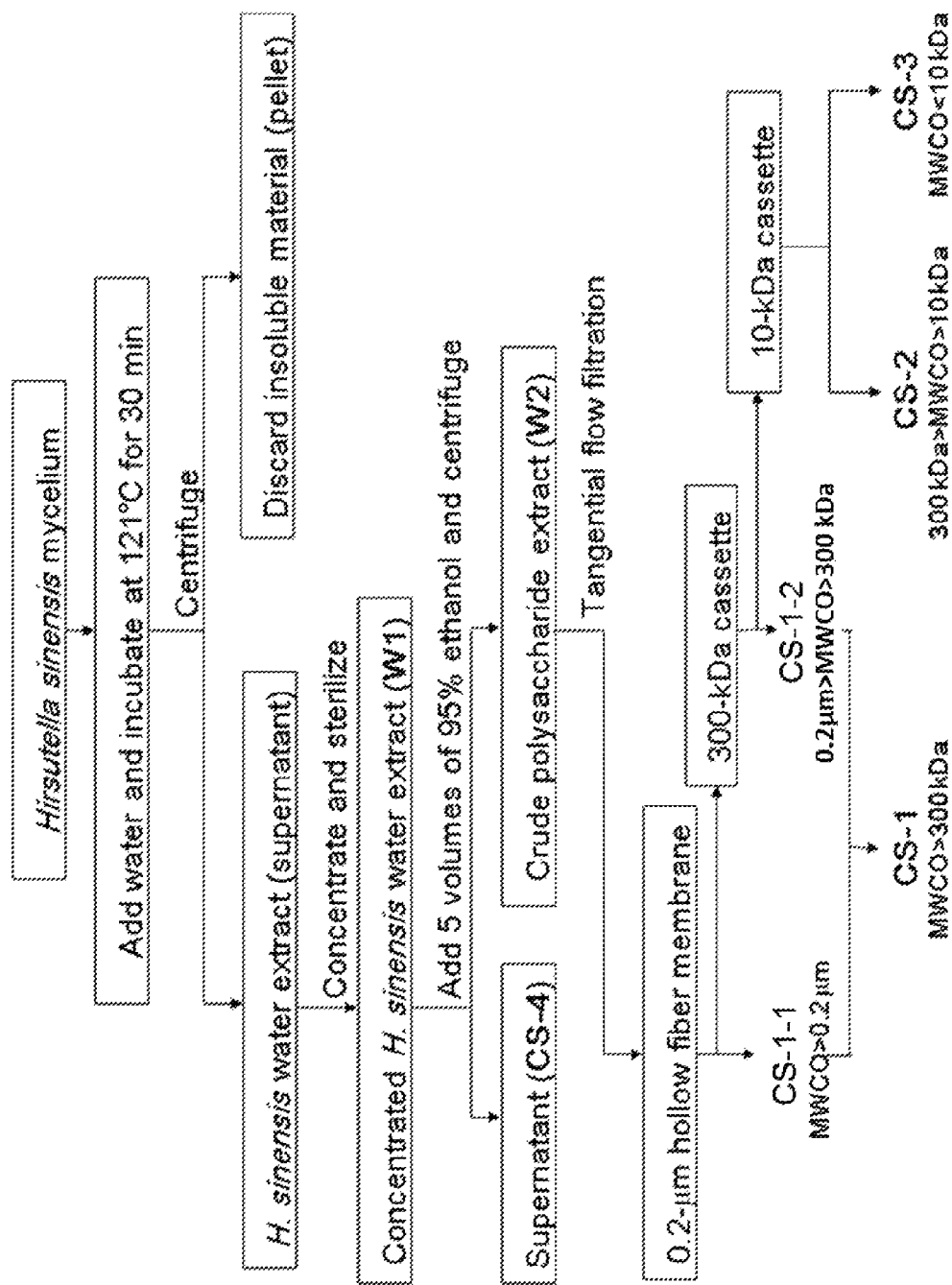
FIG. 1 shows a simplified flowchart for the isolation of *H. sinensis* water extracts and polysaccharide sub-fractions described in the present invention.

As shown in FIG. 1, a water extract is prepared by mixing 500 g of dried *H. sinensis* mycelium obtained from Chang Gung Biotechnology (Taipei, Taiwan) into 10 liters of distilled water using a 20 liter-stirred tank reactor. The 5% (w/v) mixture is agitated at a speed of 150 revolutions per minute (RPM) for 30 min at 121° C. The mixture is centrifuged to remove insoluble material. The supernatant which corresponds to a water extract of *H. sinensis* is concentrated to a final volume of 2.5 liters using a vacuum concentrator. The concentrated supernatant is sterilized at high temperature and pressure for 20 min in an autoclave to obtain a 20% (w/v) concentrated *H. sinensis* water extract (labeled as W1, see FIG. 1).

1.2 Preparation of *H. sinensis* Crude Polysaccharide Extract

Referring to FIG. 1, 120 mL of the W1 20% (w/v) concentrated *H. sinensis* water extract (which contains 2.09 g of total water-soluble carbohydrates; see Table 1) is mixed with 5 volumes (600 mL) of 95% ethanol and incubated at 4° C. for 16 hours to induce the formation of a precipitate.

The mixture is centrifuged to obtain a supernatant and a precipitate. The supernatant is removed and 120 mL of 70% ice-cold ethanol is used to wash and resuspend the precipitate (pellet) to obtain a mixture, and the mixture is centrifuged to obtain a supernatant and a precipitate. The supernatants of three washing-resuspension-centrifugation steps as described above are combined to give a supernatant of 1,040 mL (labeled as CS-4, with 0.83 g of total water-soluble carbohydrates; see Table 1). The pellet which corresponds to a crude polysaccharide extract is dissolved in 1,000 mL of distilled water and concentrated to a final volume of 700 mL using the vacuum concentrator in order to remove residual ethanol. Distilled water is added to obtain a H. sinensis crude polysaccharide extract with a final volume of 2,400 mL (labeled as W2 and containing 1.26 g of total water-soluble polysaccharides; see Tables 1 and 2).

1.3 Fractionation of H. sinensis Crude Polysaccharide Extract 2,400 mL of H. sinensis crude polysaccharide extract is placed into a beaker and incubated at 50° C. in a water bath. The extract is fractionated by using a tangential flow filtration (TFF) system (KrosFlo, Spectrum Laboratories) with a 0.2-μnm hollow fiber membrane (1,500 cm², PES). The trans-membrane pressure (TMP) is set at 15-16 psi. 600 mL of distilled water is added into the retentate during filtration when the volume of the retentate ranges from 800 to 1,000 mL. Addition of water is repeated two times (a total of 1,800 mL distilled water is added to the retentate). A 1,250 mL retentate (labeled as CS-1-1 and containing 0.24 g of total water-soluble polysaccharides) and 3,600 mL of filtrate are obtained this way.

The above-mentioned 3,600 mL of 0.2-nm membrane filtrate is placed into a beaker and incubated at 50° C. in a water bath. The filtrate is fractionated by using TFF with a 300-kDa cassette membrane (50 cm², PES). The TMP is set between 18-20 psi. 600 mL of distilled water is added into the retentate during filtration when the volume of the retentate ranges from 1,000 mL to 1,200 mL. 1,040 mL of retentate (labeled as CS-1-2, with 0.18 g of total water-soluble polysaccharides) and 3,600 mL of filtrate are obtained. Sub-fractions CS-1-1 and CS-1-2 are combined to obtain a volume of 2,290 mL (labeled as sub-fraction CS-1, which contains 0.42 g of total water-soluble polysaccharides; see Table 2).

The above-mentioned 3,600 mL of the 300-kDa filtrate is placed into a beaker and incubated at 50° C. in a water bath. The 300-kDa filtrate is fractionated using TFF with a 10-kDa cassette membrane (50 cm², PES). The TMP is set between 18-20 psi. 600 mL of distilled water is added into the retentate during filtration when the volume of the retentate is from 1,000 mL to 1,200 mL. The operation is repeated to obtain 990 mL of 10-kDa-to-300-kDa retentate (labeled as sub-fraction CS-2, which contains 0.64 g of total water-soluble polysaccharides; see Table 2) and 3,600 mL of 10-kDa filtrate (labeled as CS-3, total water soluble polysaccharides of 0.16 g; see Table 2).

The CS-1, CS-2, CS-3 and CS-4 sub-fractions are concentrated separately using a vacuum concentrator to obtain a final volume of 120 mL. Concentrated sub-fractions are sterilized at high temperature and pressure for 20 min using an autoclave.

1.4 Determination of Total Water-Soluble Carbohydrates and Polysaccharides in the H. sinensis Water Extracts and Polysaccharide Sub-Fractions The phenol-sulfuric acid assay is used to determine the level of total water-soluble carbohydrates and polysaccharides in the water extracts and polysaccharide sub-fractions isolated from H. sinensis, including: the W1 20% (w/v) concentrated H. sinensis water extract (120 mL), the W2 H. sinensis crude polysaccharide extract (2400 mL), a combination of the retentate of the 0.2-nm filtration and 300-kDa-cutoff filtration (labeled as CS-1 sub-fraction; 2,290 mL), the retentate of the 10-kDa-cutoff membrane filtration (labeled as CS-2; 990 mL), the filtrate of the 10-kDa-cutoff membrane filtration (labeled as CS-3; 3,600 mL), and the supernatants of the 95% ethanol precipitation and washing steps (labeled as sub-fraction CS-4; 1,040 mL). To establish a standard curve for the phenol-sulfuric acid assay, glucose standard solutions are prepared at concentrations of 0, 0.02, 0.04, 0.06, 0.08, 0.10, 0.12, 0.14, 0.16, 0.18, and 0.20 mg/mL. 200 μL of each solution is placed into 1.5-mL tubes. 200 μL of 5% phenol is added and the solution is mixed. 1 mL of sulfuric acid is added and the solution is mixed. After incubation for 20 min, absorbance is monitored at 490 nm using a spectrophotometer. The calibration curve of glucose standard solutions is prepared (calculated $R^2$>0.99). The sample solutions are appropriately diluted. 200 μL of each diluted solution is placed into 1.5-mL tubes. Phenol and sulfuric acid are added and absorbance is monitored as above. The values obtained are plotted onto the calibration curve of glucose standard solutions to determine the concentration of total water-soluble carbohydrates or polysaccharides of the samples.

Total water-soluble carbohydrates and polysaccharides measured in the extracts and sub-fractions isolated from H. sinensis are shown in Tables 1 and 2. The analysis in Table 2 shows that the W2 crude polysaccharide extract contains 0.42 g of total water-soluble polysaccharides with a molecular weight above 300 kDa (CS-1), which accounts for 33.3% of the total polysaccharides found in the H. sinensis crude polysaccharide extract (W2). The W2 extract also contains 0.64 g of polysaccharides between 10 kDa to 300 kDa (CS-2), which accounts for 50.8% of the total polysaccharides found in the W2 extract. The W2 extract also contains 0.16 g of polysaccharides with a molecular weight below 10 kDa (CS-3), which accounts for 12.7% of the total polysaccharides found in the W2 extract.

TABLE 1

Determination of water-soluble carbohydrates and polysaccharides in water extracts and CS-4 polysaccharide sub-fraction isolated from H. sinensis

| Fraction | | Content (g) | Percentage (%) |
|---|---|---|---|
| W1 | Total water-soluble carbohydrates | 2.09 | 100 |
| W2 | Total water-soluble polysaccharides | 1.26 | 60.3 |
| CS-4 | Mono-, di-, oligo-saccharides | 0.83 | 39.7 |

TABLE 2

Polysaccharide distribution of W2 concentrated water extract and polysaccharide sub-fractions isolated from H. sinensis

| Fraction | | Content (g) | Percentage (%) |
|---|---|---|---|
| W2 | Total water-soluble carbohydrates | 1.26 | 100 |
| CS-1 | MWCO > 300 kDa | 0.42 | 33.3 |
| CS-2 | 300 kDa > MWCO > 10 kDa | 0.64 | 50.8 |
| CS-3 | 10 kDa > MWCO | 0.16 | 12.7 |

MWCO: molecular weight cut-off 1.5 Monosaccharide Composition of the CS-1 Polysaccharide Sub-Fraction High pH anion exchange chromatography-pulsed amperometric detection (HPAEC-PAD) is used to analyze the monosaccharide composition of the CS-1 sub-fraction, which is selected here as a representative polysaccharide sub-fraction possessing insulin-sensitizing effects. Monosaccharide standard solutions of L-fucose, L-rhamnose, D-galactosamine, D-arabinose, D-glucosamine, D-galactose, D-glucose and D-mannose are prepared at 0.1, 0.5, 1, 2, and 5 mg/L. 25 µL of each solution is submitted to ionic chromatography analysis with the HPAEC-PAD Dionex ICS-5000 System (CarboPacPA1 column with an internal diameter of 4×250 mm; Thermo Scientific). Elution is performed with 16 mM NaOH (which corresponds to a mixture of water and 200 mM NaOH at the volume ratio of 92:8). The flow rate is set at 1 mL/min Temperature of column is set at 30° C. After 30 min of analysis, the peak area of each monosaccharide standard is determined and the standard curve of monosaccharide standards is prepared ($R^2 > 0.99$).

Figure 2:
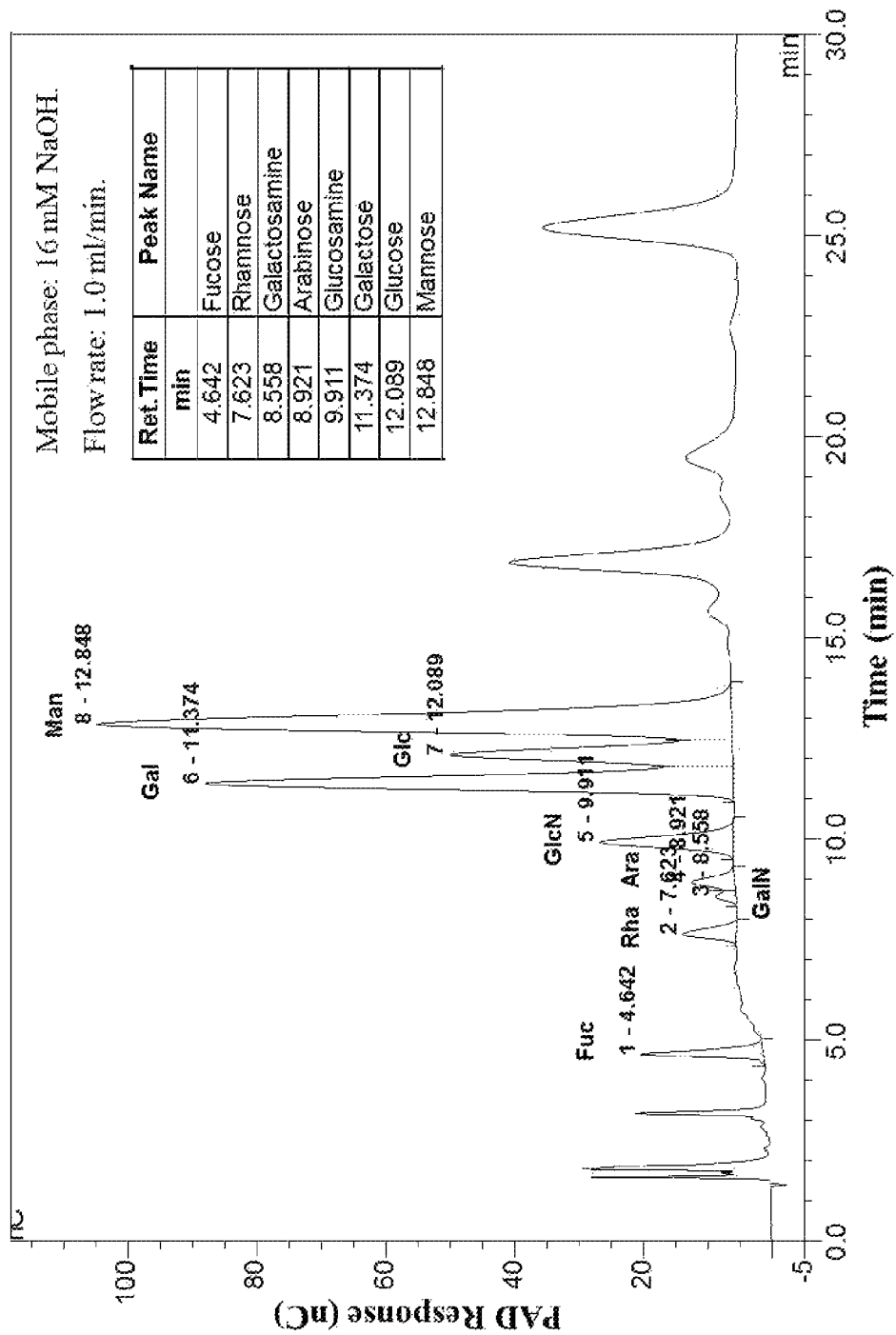
FIG. 2 shows the monosaccharide analysis of *H. sinensis* polysaccharide Sub-fraction CS-1. The analysis was performed using high-performance anion exchange chromatography with pulsed amperometric detection (HPAEC-PAD).

1 mL of CS-1 sub-fraction (3 mg of total water-soluble polysaccharides) is hydrolyzed with 1.79 mL of distilled water and 1.33 mL of trifluoroacetic acid at 112° C. for 12 hours. Acid is removed by co-distillation with water after the hydrolysis is complete. Each hydrolysate (1 mg) is dissolved in pure water (1 mg/mL). After a 4-fold dilution of the hydrolysate with pure water (0.25 mg/mL), 25 µL of the hydrolysate solution is used for ionic chromatography analysis using the HPAEC-PAD system. Elution is performed as above. After 30 min of analysis, the analytic HPAEC-PAD profile of hydrolysate solution is acquired. The monosaccharide composition and molar ratio of the CS-1 sub-fraction is determined by comparison with the standard curve. The CS-1 sub-fraction is found to contain 3.2% fucose, 3.4% rhamnose, 1.7% arabinose, 4.6% glucosamine, 23.8% galactose, 12.5% glucose, 50.4% mannose, and 0.4% galactosamine (Tables 3 and 4 and FIG. 2).

TABLE 3

Monosaccharide composition of CS-1 polysaccharide sub-fraction isolated from *H. sinensis* and analyzed using HPAEC-PAD

| Monosaccharide | Percentage (%) |
| --- | --- |
| Fucose | 3.2 |
| Rhamnose | 3.4 |
| Arabinose | 1.7 |
| Glucosamine | 4.6 |
| Galactose | 23.8 |
| Glucose | 12.5 |
| Mannose | 50.4 |
| Galactosamine | 0.4 |

TABLE 4

Monosaccharide molar ratio of CS-1 polysaccharide sub-fraction isolated from *H. sinensis*

| Monosaccharide | Molar ratio |
| --- | --- |
| Fucose | 0.07 |
| Rhamnose | 0.07 |
| Arabinose | 0.04 |
| Glucosamine | 0.09 |
| Galactose | 0.47 |
| Glucose | 0.25 |
| Mannose | 1 |
| Galactosamine | 0.01 |

1.6 Molecular Weight Distribution of CS-1 and CS-2 Polysaccharide Sub-Fractions Isolated from *H. sinensis*

The molecular weights of the CS-1 and CS-2 sub-fractions are analyzed by size-exclusion chromatography (SEC) and high performance liquid chromatography with a refractive index detector (Waters, model 2410) and a dual detector (Viscotek, model 270). Dextran 670 (1.5 mg/mL) is used as a standard marker to calibrate the system. 100 µL of sample is analyzed on two connected GPC columns (TSKgel G5000PWxL and TSKgel G6000PWxL; 7.8×300 mm) Elution is performed with 0.02% NaNO$_3$ in pure water. The flow rate is set at 0.5 mL/min (column temperature of 45° C.).

Molecular weight parameters of the CS-1 and CS-2 sub-fractions are calculated using the OmniSEC software (Viscotek) and the following equations:

Mn: number average molecular weight $$Mn = \frac{\sum NiMi}{\sum Ni}$$

Mw: weight average molecular weight $$Mw = \frac{\sum NiMi^2}{\sum NiMi}$$

Mz: higher average molecular weight $$Mz = \frac{\sum NiMi^3}{\sum NiMi^2}$$

Figure 3:
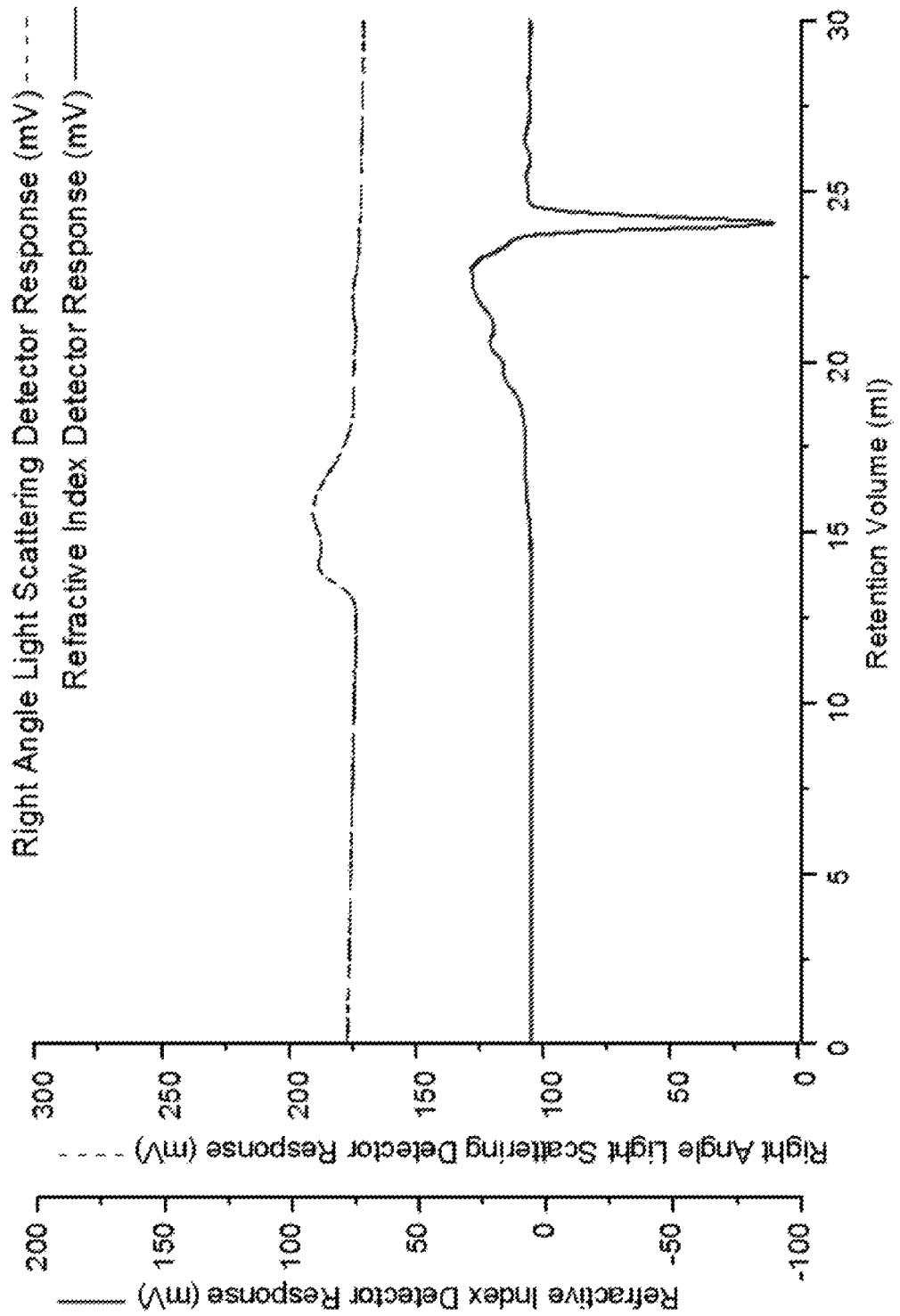
FIG. 3 shows the gel permeation chromatogram of *H. sinensis* polysaccharide sub-fraction CS-1.
Figure 4:
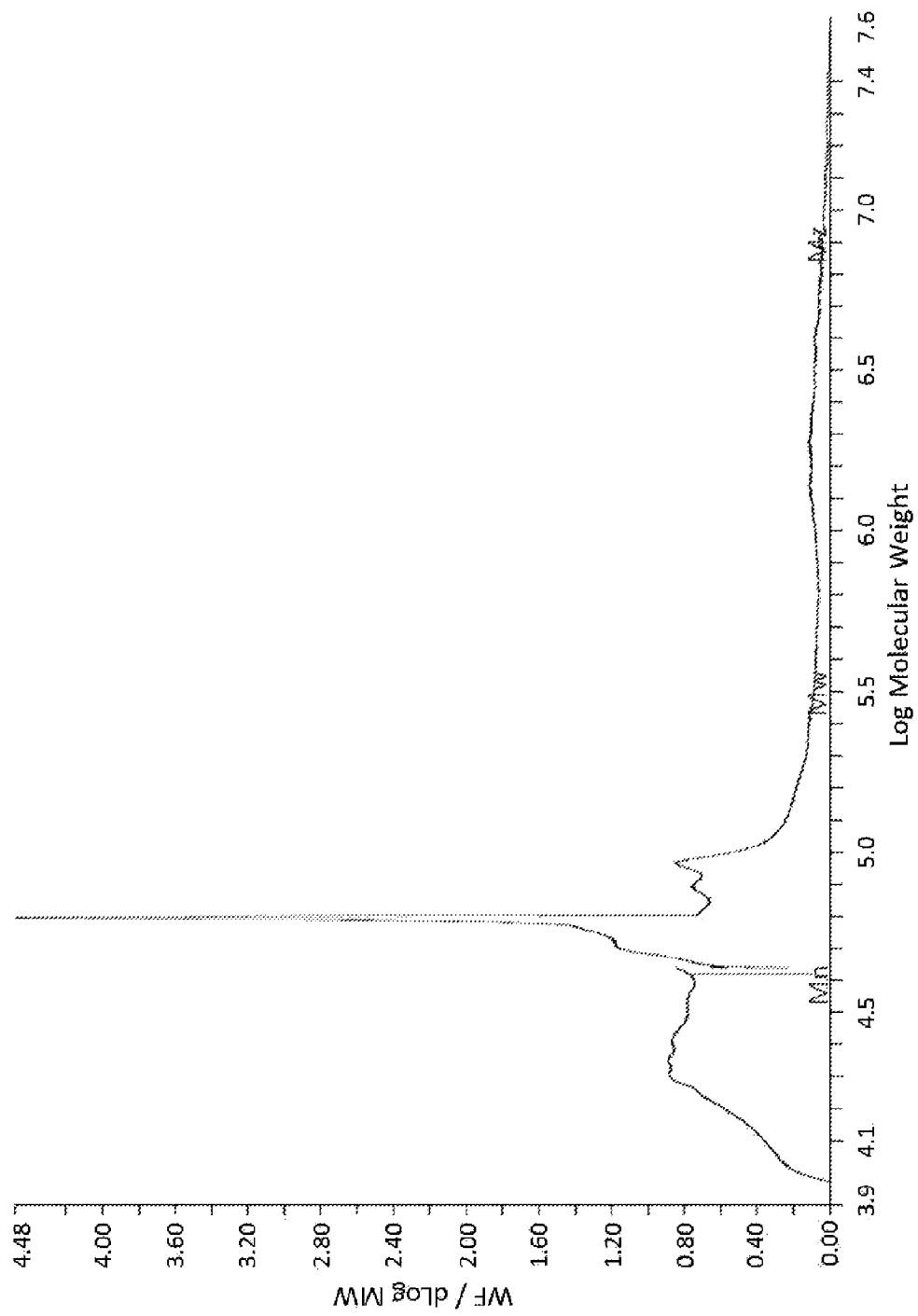
FIG. 4 depicts the graph of weight fraction (WF)/d Log molecular weight (MW) vs. log MW of *H. sinensis* polysaccharide sub-fraction CS-1.
Figure 5:
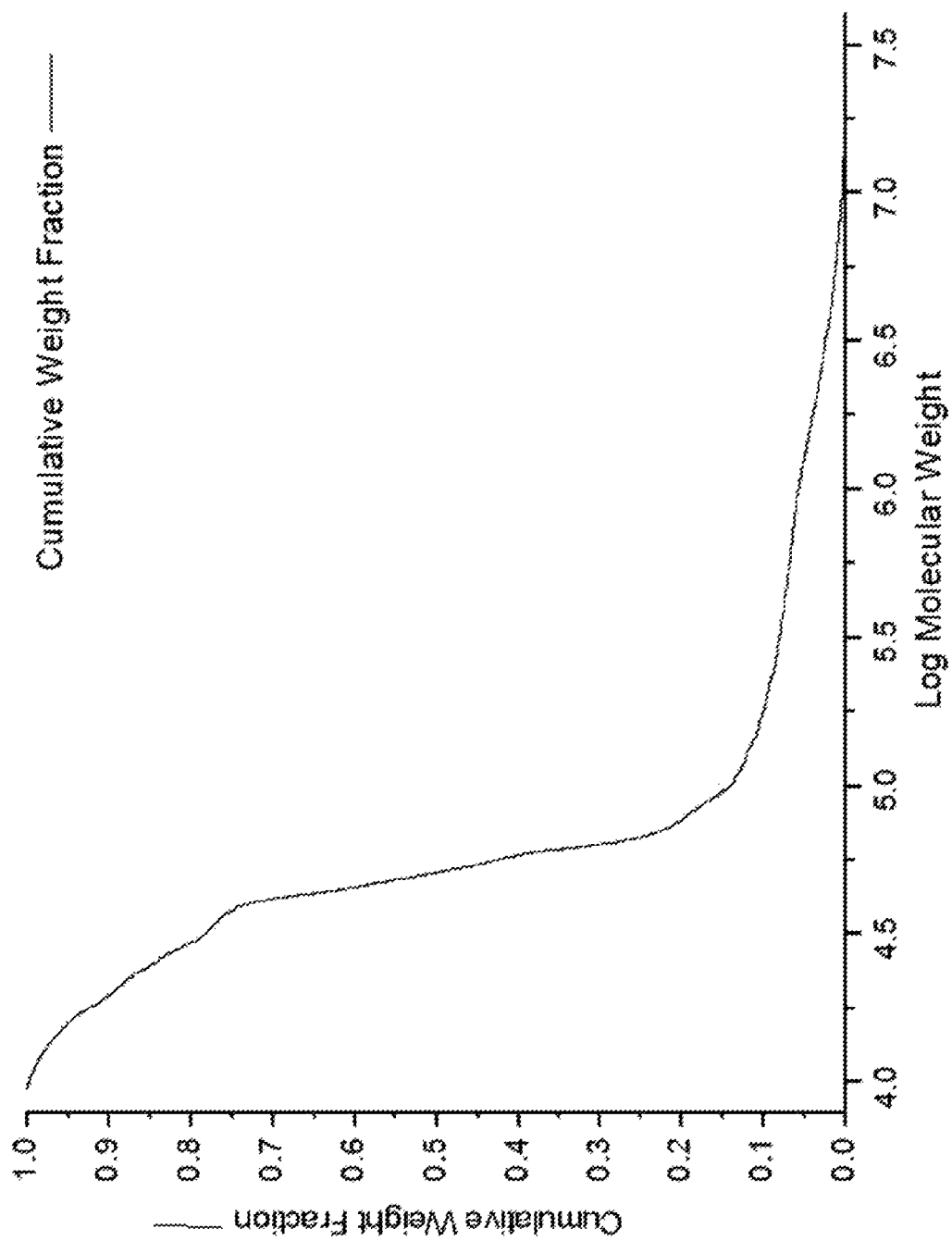
FIG. 5 shows the graph of cumulative weight fraction vs. log molecular weight of *H. sinensis* polysaccharide sub-fraction CS-1.

Mp: molecular weight at peak maximum, which is measured at the point of the molecular weight distribution maximum Mi: molecular weight of a chain Ni: number of chains of that molecular weight Molecular weight analysis of the CS-1 sub-fraction (total water-soluble polysaccharide of 4 mg/mL) is performed using the GPC/SEC system; refractive index (RI) and light scattering (LS) data are obtained (FIG. 3). The polysaccharide molecular weight distribution is calculated using Viscotek OmniSEC software (FIG. 4) and the cumulative weight fraction is determined (FIG. 5).

The cumulative weight fraction values of CS-1 at 0.95 (5%) and 0.05 (95%) correspond to molecular weights of 15,776 Da and 1,231,969 Da, respectively. Polysaccharides between 15,776 Da and 1,231,969 Da thus represent approximately 90% of total polysaccharide weight of the sub-fraction. The polydispersity index (Mw/Mn) is measured as 7.475. Table 5 shows a comparison of the molecular weights of the CS-1 and CS-2 polysaccharide sub-fractions.

TABLE 5

Molecular weight comparison of the CS-1 and CS-2 sub-fractions

| Parameter | CS-1 | CS-2 |
| --- | --- | --- |
| Mn (Daltons) | 41,731 | 38,842 |
| Mw (Daltons) | 311,921 | 49,215 |
| Mz (Daltons) | 7,589,000 | 79,949 |
| Mw/Mn (Polydispersity index) | 7.475 | 1.267 |

TABLE 5-continued

Molecular weight comparison of the CS-1 and CS-2 sub-fractions

| Parameter | CS-1 | CS-2 |
|---|---|---|
| MW of 5% of cumulative WF (Daltons) | 15,776 | 22,563 |
| MW of 95% of cumulative WF (Daltons) | 1,231,969 | 109,219 |

MW: molecular weight

Example 2

Effects of *H. sinensis* Polysaccharide Sub-Fractions on Blood Glucose Levels of HFD-Fed Mice FIG. 6A to 6D show the results of oral glucose tolerance test (OGTT) and insulin tolerance test (ITT) performed on mice fed either standard chow or HFD, and supplemented or not with the *H. sinensis* polysaccharide sub-fractions described in the present invention. C57BL/6NCrlBltw mice fed with standard chow (13.5% of energy from fat) or HFD (60% of energy from fat) are treated daily with 100 μL of polysaccharide fraction (CS-1, CS-2, CS-3, or CS-4) or distilled water by intragastric gavage for two months (n=5 mice for each group). The mouse groups consist of the following: HFD+CS-1, HFD+CS-2, HFD+CS-3, HFD+CS-4, HFD, Chow+CS-1, Chow+CS-2, Chow+CS-3, Chow+CS-4, and Chow.

Figure 6A:
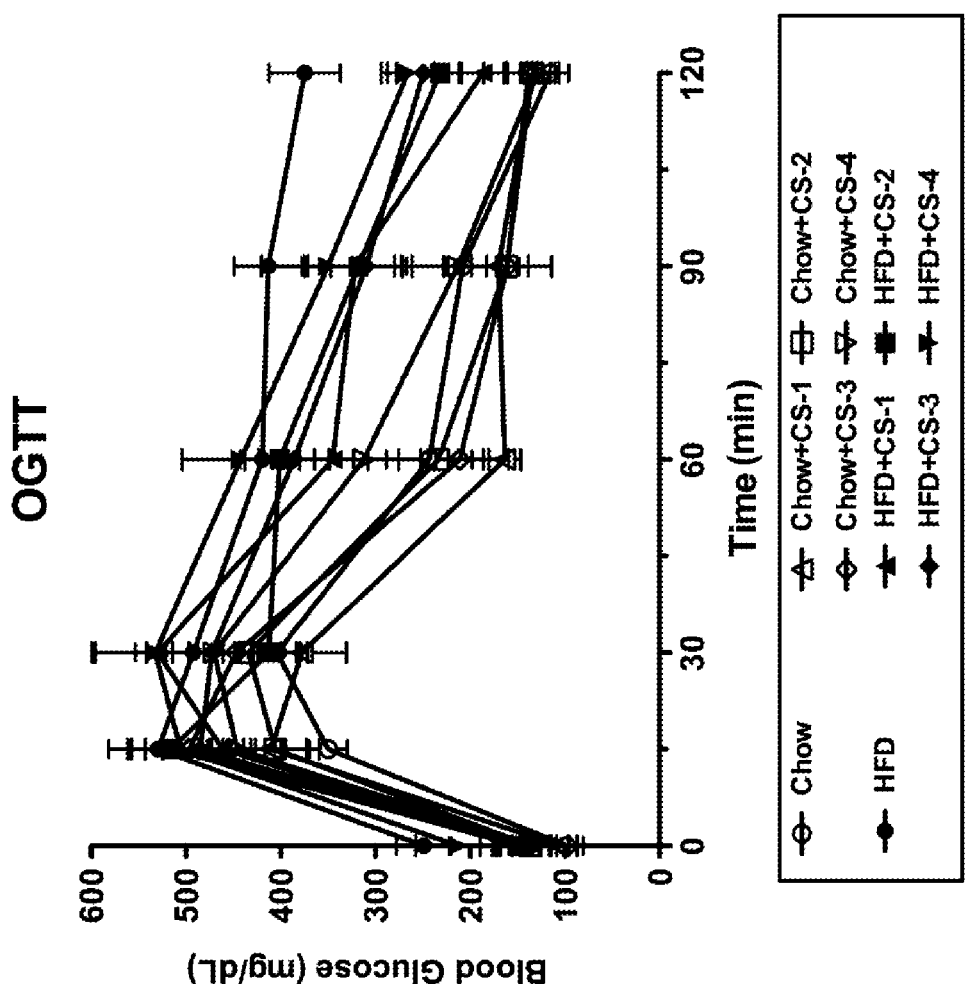
FIG. 6A shows the effects of *H. sinensis* polysaccharide sub-fractions on oral glucose tolerance test (OGTT). C57BL/6NCrlBltw mice fed with standard chow (13.5% of energy from fat) or a high-fat diet (HFD; 60% of energy from fat) are treated daily with 100 μL of polysaccharide fraction (CS-1, CS-2, CS-3 or CS-4) or distilled water by intragastric gavage for two months (n=5 mice for each group). Oral glucose challenge (3 g/kg) is administered at time 0 on fasting mice. Blood glucose is measured at the time indicated with a standard glucose meter using blood collected from the tail vein.
Figure 6B:
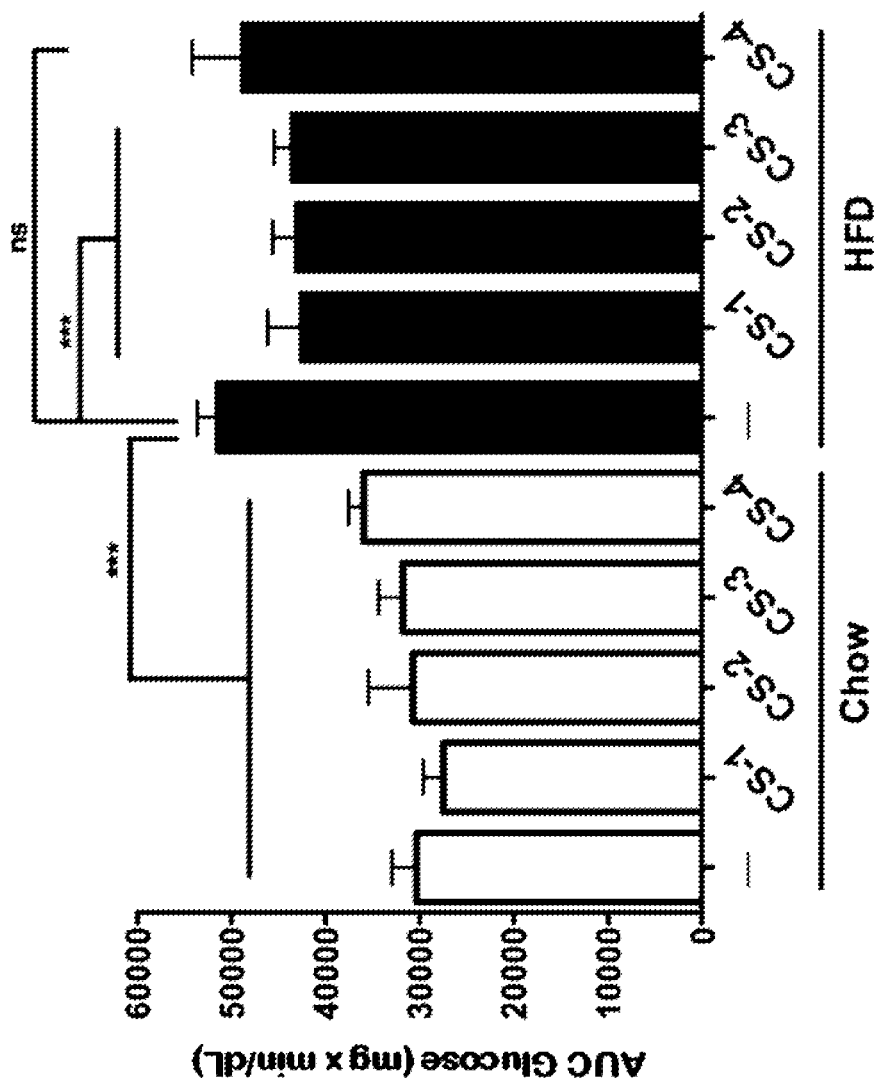
FIG. 6B shows area under the curve (AUC) determined for the oral glucose tolerance test performed in FIG. 6A. Treatment with CS-1, CS-2, and CS-3 polysaccharide sub-fractions reduces the blood sugar levels of mice fed with HFD compared with the HFD control group. Statistical significance is analyzed using Student's t test (***$P<0.001$, "ns" indicates non-significant results).
Figure 6C:
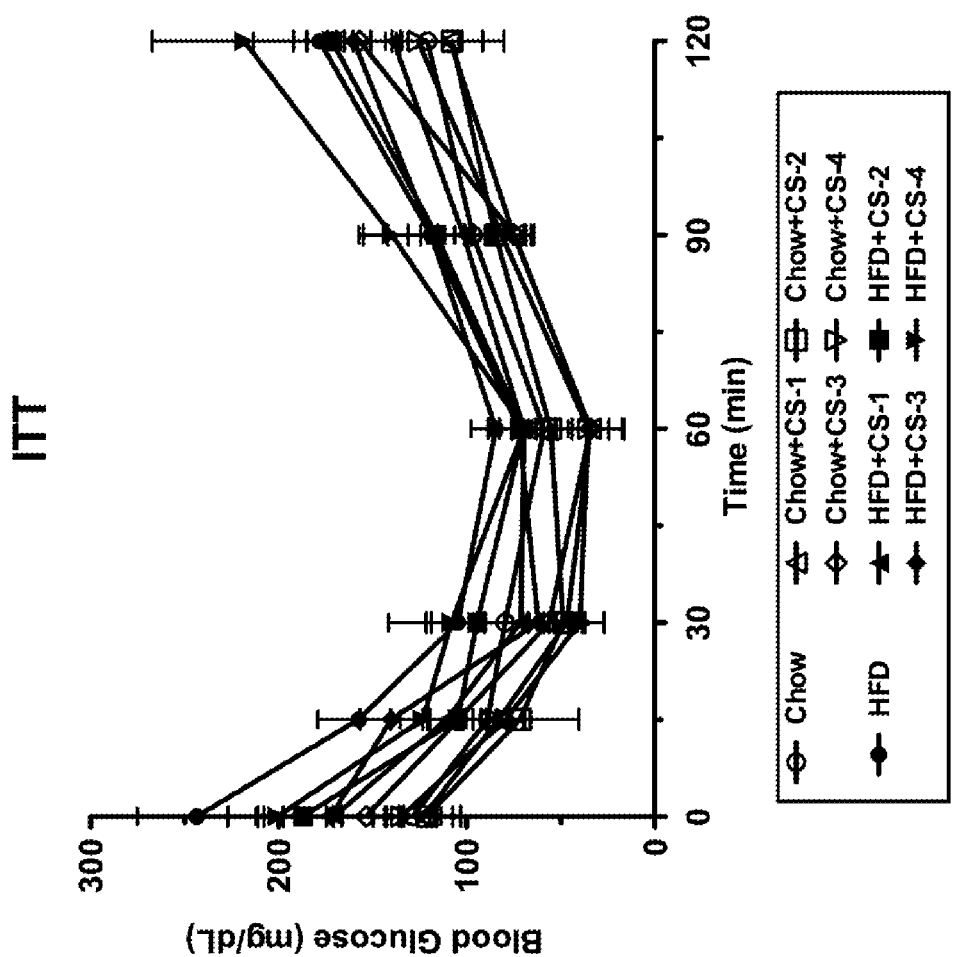
FIG. 6C shows the effects of *H. sinensis* polysaccharide sub-fractions on insulin tolerance test (ITT). C57BL/6NCrlBltw mice fed with standard chow (13.5% of energy from fat) or a high-fat diet (HFD; 60% of energy from fat) are treated daily with 100 μL of polysaccharide fraction (CS-1, CS-2, CS-3 or CS-4) or distilled water by intragastric gavage for two months (n=5 mice for each group). Blood glucose levels of the mice are monitored following an insulin challenge (1 unit/kg) administered intraperitoneally at time 0.
Figure 6D:
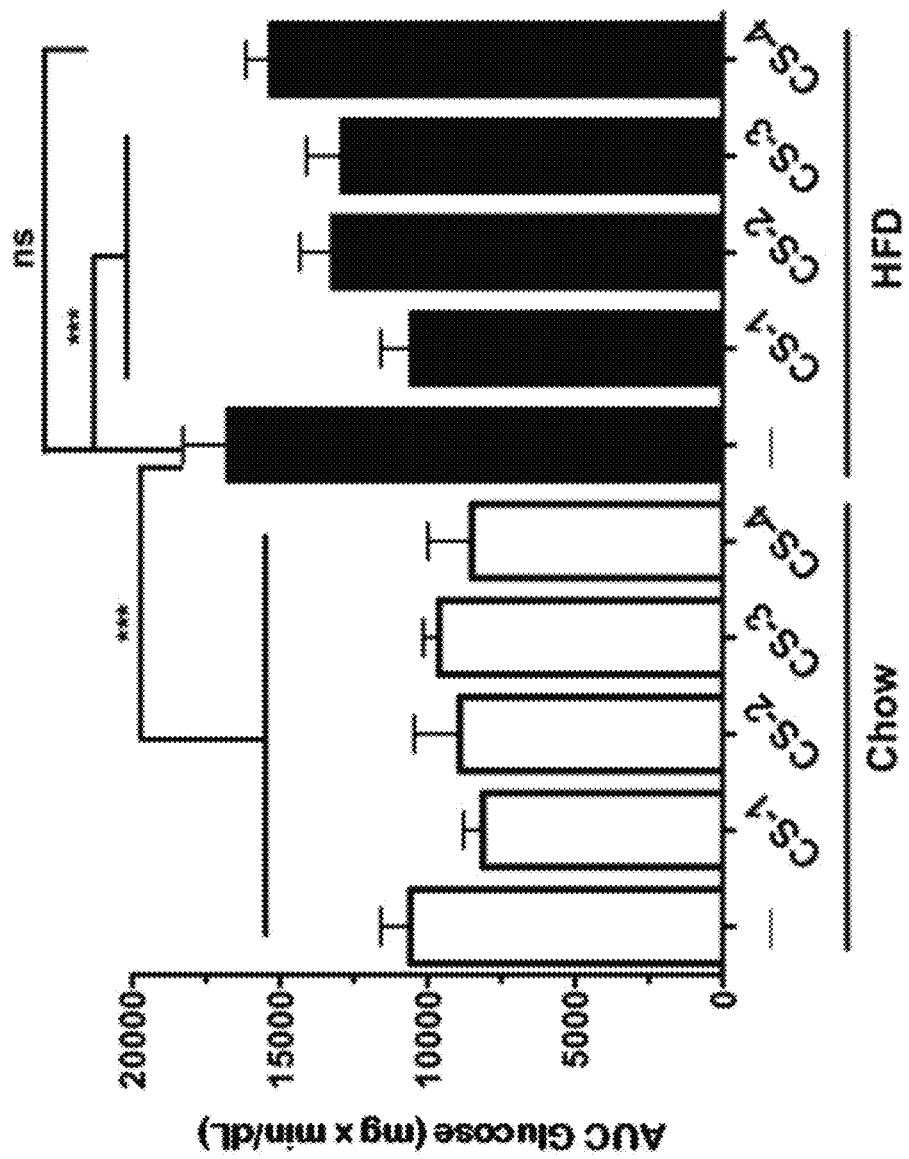
FIG. 6D shows area under the curve (AUC) determined for the insulin tolerance test performed in FIG. 6C. Treatment with CS-1, CS-2, and CS-3 polysaccharide sub-fractions reduces the blood sugar levels of mice fed with HFD compared with the HFD control group. Statistical significance is analyzed using Student's t test (***$P<0.001$, "ns" indicates non-significant results).

As shown in FIGS. 6A and 6B, the blood glucose levels of fasting HFD-fed mice submitted to OGTT are higher than those of fasting Chow-fed mice. Notably, FIGS. 6A and 6B show that treatment with CS-1, CS-2 and CS-3 polysaccharide sub-fractions reduces blood glucose levels in HFD-fed mice submitted to OGTT compared to control HFD mice. These results indicate that CS-1, CS-2 and CS-3 sub-fractions produce insulin-sensitizing effects. On the other hand, the sub-fraction CS-4 produces no statistically significant insulin-sensitizing effects. Similarly, FIGS. 6C and 6D show that blood glucose levels of fasting HFD-fed mice submitted to ITT are higher than those of fasting Chow-fed mice, an observation which suggests that the HFD-fed mice show lower sensitivity to insulin compared to Chow-fed mice. Treatment with CS-1, CS-2 and CS-3 polysaccharide sub-fractions reduces blood glucose levels in HFD-fed mice submitted to ITT compared to control HFD mice (FIGS. 6C and 6D). These results confirm that CS-1, CS-2 and CS-3 sub-fractions produce insulin-sensitizing effects.

Based on the concentration of polysaccharides found in each sub-fraction (CS-1, 0.35 g/100 mL; CS-2, 0.53 g/100 mL; CS-3, 0.13 g/100 mL), we calculate the effective amount of polysaccharide sub-fraction that produces insulin-sensitizing effects in the treated mice (which have an average body weight of 30 g): 0.00035 g of CS-1/mouse; 0.00053 g of CS-2/mouse; and 0.00013 g of CS-3/mouse. By extension, the effective dosage of *H. sinensis* polysaccharide sub-fraction producing insulin-sensitizing effects in a human subject (with a body weight of 70 kg) is calculated as follows: 0.82 g of CS-1/subject; 1.24 g of CS-2/subject; and 0.30 g of CS-3/subject. In other words, the effective dosage of *H. sinensis* polysaccharide sub-fraction in a human subject is: 0.012 g/kg (CS-1), 0.018 g/kg (CS-2), and 0.0043 g/kg (CS-3).

The present invention provides *H. sinensis* polysaccharide sub-fractions, which can reduce hyperglycemia and enhance insulin sensitivity in mammals. The *H. sinensis* polysaccharide sub-fractions of the present invention are therefore valuable for the industry to develop new preventive strategies and treatments for type 2 diabetes mellitus, insulin resistance, and metabolic syndrome. The embodiments presented in the present disclosure are given as representative results that can be obtained with the polysaccharide sub-fractions, but they do not, however, limit the scope of the invention. It will be apparent to those skilled with the art that modifications can be made to the embodiments, without departing from the scope of the present invention and the appended claims.

What is claimed is:

1. A method for improving insulin sensitivity, comprising administering an effective amount of a polysaccharide extracted from *Hirsutella sinensis* to a subject, wherein the polysaccharide is isolated from a water extract of a *H. sinensis* mycelium and contains at least mannose, glucose, and galactose at a weight ratio ranging from 50:12:23 to 51:13:24.

2. The method of claim 1, wherein the polysaccharide further contains fucose, rhamnose, arabinose, glucosamine, and galactosamine.

3. The method of claim 2, wherein a weight ratio of the fucose, rhamnose, arabinose, glucosamine, galactose, glucose, mannose, and galactosamine ranges from 3:3:1:4:23:12:50:0.2 to 4:4:2:5:24:13:51:0.6.

4. The method of claim 1, wherein the polysaccharide has a molecular weight ranging from 15,776 Da to 1,231,969 Da, and a polydispersity index (Mw/Mn) of 7.475.

5. The method of claim 1, wherein an average molecular weight of the polysaccharide is 312 kDa.

6. The method of claim 1, wherein the polysaccharide reduces fasting and postprandial blood glucose levels of the subject.

7. The method of claim 1, wherein the polysaccharide reduces insulin resistance of the subject.

8. The method of claim 1, wherein the effective amount of the polysaccharide is from 0.001 mg/kg to 1 g/kg.

9. The method of claim 1, wherein the effective amount of the polysaccharide is 0.0646 g per kilogram of body weight.

* * * * *